United States Patent [19]

Byker

[11] Patent Number: 5,294,376

[45] Date of Patent: Mar. 15, 1994

[54] BIPYRIDINIUM SALT SOLUTIONS

[75] Inventor: Harlan J. Byker, Zeeland, Mich.

[73] Assignee: Gentex Corporation, Zeeland, Mich.

[21] Appl. No.: 720,170

[22] Filed: Jun. 25, 1991

[51] Int. Cl.$^5$ .................. C07D 401/04; C09K 9/00; G02B 5/30; G02F 1/01; G02F 1/137
[52] U.S. Cl. ................................ 252/600; 359/265; 359/839; 546/257; 252/582
[58] Field of Search ............. 359/265, 839; 546/257; 252/600

[56] References Cited

U.S. PATENT DOCUMENTS

| | | | |
|---|---|---|---|
| 3,118,891 | 1/1964 | Kramer | 546/257 X |
| 3,340,041 | 9/1967 | Homer et al. | 546/257 X |
| 3,652,149 | 3/1972 | Rogers | 546/257 X |
| 3,697,528 | 10/1972 | Andrews et al. | 546/257 X |
| 3,856,714 | 12/1974 | Moore et al. | 546/257 X |
| 3,912,368 | 10/1975 | Ponjee et al. | 546/257 X |
| 4,841,058 | 6/1989 | Endo et al. | 546/257 |
| 4,902,108 | 2/1990 | Byker | 359/839 X |

FOREIGN PATENT DOCUMENTS

| | | | |
|---|---|---|---|
| 61-148162 | 7/1986 | Japan | 546/257 |
| 61-203191 | 7/1986 | Japan | 546/257 |

*Primary Examiner*—Floyd D. Higel
*Attorney, Agent, or Firm*—Foley & Lardner

[57] ABSTRACT

The present invention provides solutions of certain 4,4'-bipyridinium salts, such as salts of 1,1'-dibenzyl-2,2',6,6'-tetraalkyl-4,4'-bipyridinium cations. The solutions of the invention are employed as solutions of variable transmittance in solution-phase electrochromic devices, including such devices that are single-compartment and self-erasing. In the solutions of the invention in such devices, the bipyridinium salts are cathodic electrochromic compounds, as reduction of a cation of such a salt causes its molar extinction coefficient at at least one wavelength in the visible range to increase markedly. Electrochromic devices, in which solutions of the invention provide variable transmittance, are, in turn, components of variable transmittance in display devices, windows and other types of light filters, and variable reflectance mirrors, such as those that can be used as dimmable rearview mirrors in motor vehicles.

57 Claims, 2 Drawing Sheets

BIPYRIDINIUM SALT SOLUTIONS

TECHNICAL FIELD

The present inventions concerns novel solutions, coursing certain bipyridinium salts, as media of variable transmittance novel electrochromic devices and novel uses of the devices, such as components of variable transmittance in variable-reflectance, rearview motor-vehicle mirrors.

BACKGROUND OF THE INVENTION

In electrochromic devices, the color or darkness of a composition is changed by an electrochemical reaction caused by application of an electrical potential difference to electrodes in contact with the composition. Electrochromic devices long have been of interest for providing varying displays in display devices of various types, varying transmittance in variable transmittance lights filters, such as windows, and varying reflectance in variable reflectance mirrors.

In a solution-phase electrochromic device, at least one substance, which changes color or absorbance to light in the visible wavelength range in an electrochemical reaction in operation of the device, is in a solution in the device both at equilibrium with no potential applied to cause an electrochemical reaction and when reduced (if the substance is "cathodic," i.e., electrochemically reduced in the device) or oxidized (if the substance is "anodic," i.e., electrochemically oxidized in the device).

One type of solution phase electrochromic device is a single-compartment, solution-phase, self-erasing electrochromic device. U.S. Pat. No. 4,902,108 (hereinafter the U.S. Pat. No. '108), the entire disclosure of which is incorporated herein by reference, describes a class of such solution-phase electrochromic devices. The U.S. Pat. No. '108 also describes solutions for use as the media of reversibly variable transmittance in such devices; "cathodic" compounds, which undergo a color change on electrochemical reduction in such devices; and "anodic" compounds, which undergo a color change on electrochemical oxidation in such devices. In the devices of the U.S. Pat. No. '108, the reduced cathodic compound and oxidized anodic compound remain in solution and react with each other to regenerate the zero-potential equilibrium forms of both compounds. Further, the U.S. Pat. No. '108 describes the use of the electrochromic devices of the Patent as the components of varying color or darkness in various display devices; the components of reversibly variable transmittance in light filters, such as windows; and the components of reversibly variable transmittance in variable reflectance mirrors, such as dimmable, rearview mirrors for motor vehicles.

In a single-compartment, self-erasing, solution-phase electrochromic device, such as those of the U.S. Pat. No. '108, a solution comprising a cathodic compound and an anodic compound is held in contact with two electrodes. Preferably the solution is held as a layer of solution between and in contact with two, substantially planar, parallel, spaced-apart electrode layers. These electrode layers may be substantially transparent layers (such as of indium-tin oxide or fluorine-doped tin oxide) coated on a substantially transparent material, such as glass. With no potential difference between the electrode layers, and the solution therebetween in its zero-potential equilibrium state, the solution can be clear or slightly colored. When a potential difference of sufficient magnitude (which will typically be less than about 2.0 volts and will depend on a number of factors, including the reduction potentials of the cathodic and anodic compounds in the solution) is applied to the electrode layers (and across the solution therebetween), transmittance of light through the device is reduced, and the color of the device may be perceived as changing, as reduction of cathodic compound at the electrode functioning as the cathode yields a composition with a molar extinction coefficient at at least one wavelength in the visible range that is higher than that of the cathodic compound in its zero-potential equilibrium state and, similarly, oxidation of anodic compound at the electrode functioning as the anode yields a composition with a molar extinction coefficient at at least one wavelength in the visible range that is higher than that of the anodic compound in its zero-potential equilibrium state. The rate at which the solution layer darkens or changes color once a potential difference is applied to the electrode layers, and the steady-state darkness or color that results if a potential difference is maintained for a sufficiently long period of time, will depend on a number of factors, including the potential difference, the current across the solution layer, the thickness of the solution layer, and the rate at which reduced cathodic compound is re-oxidized and oxidized anodic compound is re-reduced (e.g., in the case of cathodic compound, by reaction of the reduced cathodic compound with oxided anodic compound in the solution). Once the potential difference between the electrode layers is reduced or eliminated, the color or darkness of the solution layer will return toward its zero-potential equilibrium state, as the concentrations of reduced cathodic compound and oxidized anodic compound will decrease toward lower, steady-state levels. Thus, by adjusting the potential difference between the electrode layers, such a device can function as a "gray-scale" device, with continuous, or step-wise, variable transmittance over a wide range. Ideally, when the potential between the electrodes of such a device is returned to zero, the device spontaneously returns to the same, zero-potential, equilibrium color and transmittance as the device had before the potential was applied.

Approaching this ideal sufficiently closely to make the use of single-compartment, solution-phase, self-erasing electrochromic devices commercially feasible has been a problem. Thus, in most applications of such devices, the cycle-life of the devices (the number of times the potential between the electrodes can be applied and removed without unacceptable degradation in the device, e.g., in the color or darkness of the device in the zero-potential, equilibrium state or the steady state at a selected potential difference) is an important factor and presents a formidable problem. In practical applications, the anodic and cathodic compounds in a solution must be stable to many thousands of cycles of oxidation and reduction.

In applications of single-compartment, solution-phase, self-erasing electrochromic devices in mirrors and windows, a significant problem is stability of the components of the solutions of reversibly variable transmittance in the devices to violet and ultraviolet (UV) light. Thus, when the device is activated (i.e, a potential is placed across the solution of the device sufficient to cause coloration), the performance of the device is typically degraded on exposure of the solution to violet and ultraviolet light. The degraded performance manifests itself as residual color formation in the device, which does not clear up when the device returns to its zero-potential, equilibrium state, and as a decrease in the darkness of coloration attainable with the device when it is activated. Thus high-end (at low or no potential difference) transmission or reflectance of a window or mirror, respectively, is undesirably decreased and the low-end (at significant potential difference with substantially reduced transmittance) transmission or reflectance that can be achieved is undesirably increased.

Under most modes of operation, dimmable rearview mirrors for motor vehicles, which use solution-phase electrochromic devices to provide variable reflectance and their dimming effect, are only colored or dimmed (darkened) at night when light from the headlamps of following vehicles can pose a glare problem for drivers. At night the amount of violet or ultraviolet radiation reaching the solution of the device is insufficient to cause significant degradation over the expected life of the rearview mirror device. However, even in the zero-potential, equilibrium state, solution-phase devices, such as those of the U.S. Pat. No. '108, are slowly degraded by exposure of the solution of the devices to ultraviolet light. This slow degradation process is of particular concern with outside rearview mirrors on motor vehicles since they may be exposed to sunlight containing ultraviolet light day after day over a number of years. In fact, in electrochromic devices which are variable transmittance components of outside, dimmable, rearview motor vehicle mirrors and contain electrochromic solutions according to the U.S. Pat. No. '108 as media of variable transmittance, the electrochromic solutions do degrade over a period of several months to a year to the point where they become unacceptable for outside dimmable rearview mirror use.

Attempts to solve the problem of instability to exposure to ultraviolet ("UV") light have included the use of screens or barriers to UV light, to intercept UV-light before it reaches the solution of the electrochromic device, or the inclusion, in the solution of reversibly variable transmittance in the device, of UV-stabilizing compounds. The UV-stabilizing compounds that have been used have been developed to stabilize organic compositions (e.g., plastics) against degradation by exposure to UV light. The use of screens or barriers of UV-light-absorbing material adds significantly to the cost of materials for electrochromic devices and significantly complicates the manufacture of such devices by requiring that the screen or barrier be incorporated into the device while avoiding undesirable optical effects that may accompany such incorporation. The use of UV-stabilizing compounds in solutions of reversibly variable transmittance in electrochromic devices, while in many cases capable of increasing the useful life of the devices by retarding photodegradation in the solutions exposed to UV light while in their zero-potential equilibrium state, are not totally effective in eliminating this UV-induced photochemical degradation. Further, the degradative products that do form in the solutions when UV-stabilizing compounds are present significantly reduce the useful cycle life of the devices when they are cycled between the clear and colored state, even, e.g., at night, in the absence of light which might cause additional photochemical degradation during cycling. Thus, a problem confronting the art of solution-phase electrochromic devices, including single-compartment, solution-phase, self-erasing electrochromic devices, is to identify compounds which are suitable for use as anodic or cathodic compounds in the solutions of reversibly variable transmittance in such devices and that render such solutions, at least in their zero-potential equilibrium states, highly stable to exposure to ultraviolet light from e.g. sunlight.

There are a number of other desireable characteristics in anodic or cathodic compounds for use in solutions of variable transmittance in solution-phase electrochromic devices, including those which are single-compartment and self-erasing. Such compounds are desirably stable in solution by themselves and in combination with each other in their zero-potential equilibrium states even at high temperatures above about 80° C. and preferably up to about 120° C. The anodic and cathodic compounds in their colored or activated states in solution should be stable at at least 50° C. and preferably at at least 75° C., so that devices containing solutions of the compounds can be cycled without significant degradation between their colorless and colored states at at least 50° C. and preferably at at least 75° C. Anodic and cathodic compounds for media of variable transmittance in electrochromic devices which need to operate over a large range in transmittance or reflectance, as in high quality, dimmable rearview mirrors for motor vehicles, should be colorless or nearly colorless in their zero-potential equilibrium state, undergo a large increase in molar extinction coefficient in the visible range on oxidation or reduction, and be soluble enough to provide for the range of transmittance or reflectance required in the device in which a solution of the compound is employed to provide variable transmittance.

A particularly preferred solution for use as the medium of reversibly variable transmittance in a single-compartment, solution-phase, self-erasing electrochromic device, used to provide variable reflectance in a variable reflectance rearview mirror for a motor vehicle, consists of propylene carbonate as solvent, benzylviologen difluoroborate (i.e., 1,1'-dibenzyl-4,4'-bipyridinium difluoroborate) as cathodic compound at 5 mM –50 mM in the solution at room temperature, 5,10-dihydro-5,10-dimethyl phenazine as anodic compound at 5 mM –50 mM in the solution at room temperature, 1–10% (w/w) polymethylmethacrylate to thicken the solution, and ethyl 2-cyano-3,3-diphenyl acrylate at 200 mM to 700 mM in the solution at room temperature to somewhat retard UV-associated photodegradation in the solution in its zero-potential equilibrium state. This system of compounds fits the stability, color and solubility criteria discussed above. However, for long lived outside rearview mirrors, especially outside rearview mirrors on automobiles, and certain window applications, very high stability against long term exposure to sunlight is required while the device is colorless or unactivated. A problem remains with the above system of compounds: slow degradation in sunlight, with the degradation products that form adversely affecting the cycle life of the devices containing the systems of compounds.

Salts of 4,4'-bipyridinium dications, in addition to the well known viologen salts, derivatized at the 1 and 1' positions are known. See Emmert and Varenkamp, Chemishe Berichte 56B, 491–501 (1923); and Sugiyama et al., Japanese Patent Application Publication No. 61-148,162 (1986). There have been no reports suggesting the use, or the advantages of using, salts of 4,4'-bipyridinium dications derivatized at 1 or 1' position with alkyl, phenyl or benzyl, and at at least one of the 2,2',6 and 6' positions with alkyl as cathodic compounds in solutions of reversibly variable transmittance in solution-phase electrochromic devices.

SUMMARY OF THE INVENTION

It has been discovered unexpectedly that salts of certain 4,4'-bipyridinium dications, derivatized at the and 1' positions with alkyl, phenyl or benzyl and at at least one of the 2, 2', 6 and 6' positions with alkyl, can be employed advantageously as cathodic compounds in solutions of variable transmittance in solution-phase electrochromic devices.

The properties of such bipyridinium salts, including their solubilities, and the properties of solutions of the salts with anodic compounds, including stability to high temperature, cycling between zero (or low) and high (up to about 2 volt) potentials, and stability to UV-exposure, make the solutions especially useful as media of reversibly variable transmittance in solution-phase electrochromic devices. The devices, in turn, can advantageously be employed in practical applications such as components of reversibly variable transmittance in dimmable, inside and outside, rearview mirrors for motor vehicles.

More particularly, we have discovered that difficult to oxidize anions, like $BF_4^-$, $PF_6^-$ and $ClO_4^-$, provide colorless salts with 1,1'-dibenzyl and dialkyl-4,4'-bipyridinium dications, which salts are adequately soluble in polar organic solvents to allow for substantial ranges in transmittance and reflectance in electrochromic devices utilizing solutions of these salts. In addition, we have discovered that salts of this type in their zero-potential, equilibrium states are stable in solution at at least 100° C., can be cycled back and forth between their reduced, colored, cation radical state and oxidized, dication state at at least 50° C. for many thousands of cycles without signs of degradation. Most remarkably, we have discovered that using a salt of the 1,1'-dibenzyl-2,2'6,6,-tetramethyl-4,4'-bipyridinium dictation as the cathodic material in a solution-phase electrochromic device dramatically increases the UV stability of the solutions of these devices. Similar improvement in UV stability has also been discovered with solutions containing other 4,4'-bipyridinium dictations substituted with alkyl groups in at least some of the positions ortho to the pyridine nitrogens.

DETAILED DESCRIPTION OF THE INVENTION

Figure 1:
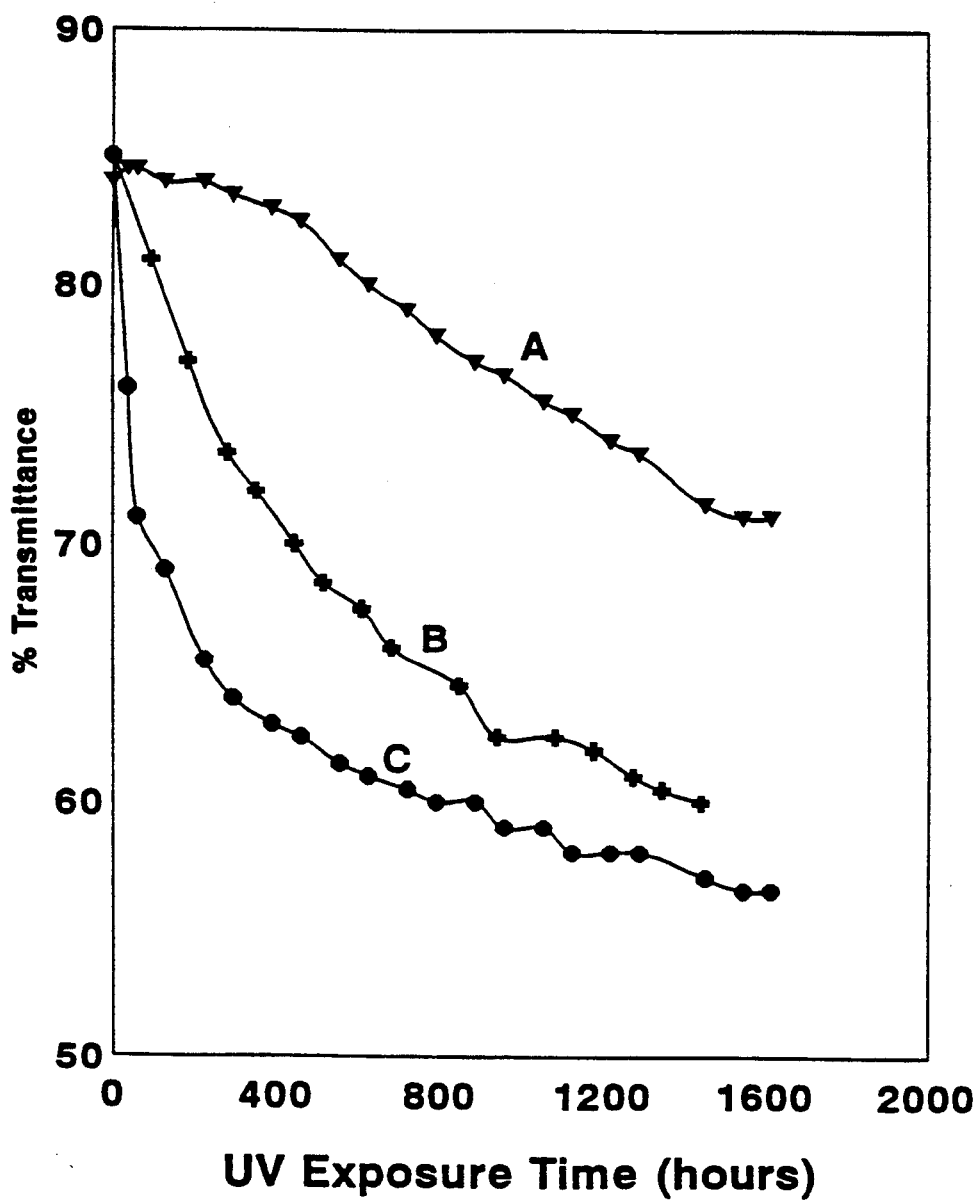
FIG. 1 is a graph illustrating the stabilities to exposure to ultraviolet radiation of solutions of 5,10-dihydro-5,10-dimethylphenazine with three different 4,4'-bipyridinium cathodic electrochromic compounds: 1,1'-dibenzyl-2,2',6,6'-tetramethyl-4,4'-bipyridinium difluoroborate (Curve A), 1,1'-dibenzyl-2,2'-dimethyl-4,4'-bipyridinium difluoroborate (Curve B) and 1,1'-dibenzyl4,4'-bipyridinium difluoroborate (Curve C).

In one of its aspects, the present invention is a solution which comprises a solvent; an anodic electrochromic compound which, upon oxidation of its zero-potential equilibrium state, undergoes an increase in molar extinction coefficient at at least one wavelength in the visible range; and a cathodic electrochromic compound which is a salt of a cation of Formula IV

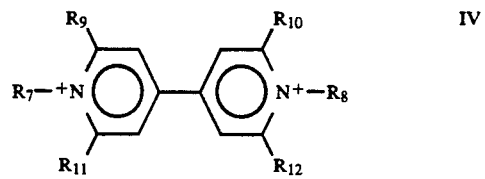

wherein $R_7$ and $R_8$ are independently selected from the group consisting of an alkyl group with 1-20 carbon atoms, phenyl and benzyl; and $R_9$, $R_{10}$, $R_{11}$, and $R_{12}$ are independently selected from the group consisting of hydrogen and an alkyl group with 1-4 carbon atoms, provided that at least one of $R_9$, $R_{10}$, $R_{11}$, and $R_{12}$ is an alkyl group.

In another of its aspects, the invention is a solution which is liquid at room temperature and comprises a solvent and a salt of a cation of Formula XVII

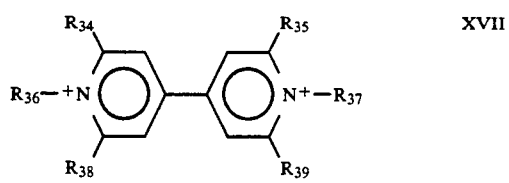

wherein $R_{36}$ and $R_{37}$ are independently selected from the group consisting of benzyl, phenyl, and alkyl of 1-20 carbon atoms; and $R_{34}$, $R_{35}$, $R_{38}$ and $R_{39}$ are independently selected from the group consisting of hydrogen and alkyl groups of 1-4 carbon atoms, provided that at least three of $R_{34}$, $R_{35}$, $R_{38}$ and $R_{39}$ are alkyl.

The solutions of the invention, by the presence of the salts of the cations of Forumla IV or XVII, are improved solutions for use as media of variable transmittance in solution-phase electrochromic devices.

Still further, the invention entails a solution-phase electrochromic device in which the solution of variable transmittance comprises a solvent; an anodic electrochromic compound which, upon oxidation of its zero-potential equilibrium state, undergoes an increase in molar extinction coefficient at at least one wavelength in the visible range; and a cathodic electrochromic compound which is a salt of a cation of Formula IV

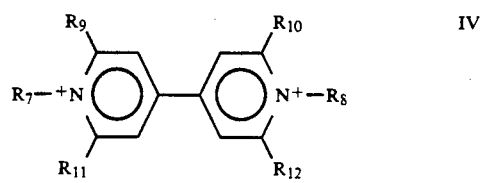

wherein $R_7$ and $R_8$ are independently selected from the group visible range; and a cathodic electrochromic compound which and benzyl; and $R_9$, $R_{10}$, $R_{11}$, and $R_{12}$ are independently selected from the group consisting of hydrogen and an alkyl group with 1-4 carbon atoms, provided that at least one of $R_9$, $R_{10}$, $R_{11}$, and $R_{12}$ is an alkyl group.

In still a further aspect, the invention entails a solution-phase electrochromic device in which the solution of variable transmittance comprises a solvent, which is a liquid at room temperature, and a salt of a cation of Formula XVII

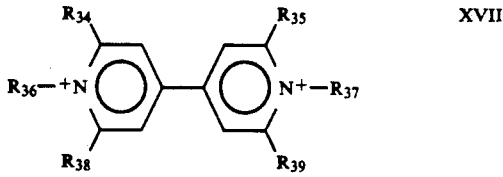

wherein $R_{36}$ and $R_{37}$ are independently selected from the group consisting of benzyl, phenyl, and alkyl of 1-20 carbon atoms; and $R_{34}$, $R_{35}$, $R_{38}$, and $R_{39}$ are independently selected from the group consisting of hydrogen and alkyl groups of 1-4 carbon atoms, provided that at least three of $R_{34}$, $R_{35}$, $R_{38}$, and $R_{39}$ are alkyl.

Still further the invention entails display devices, variable transmittance light filters, and variable reflectance mirrors which comprise, as components of variable transmittance, devices of the invention.

The solvents that can be employed in the solutions of the invention include those well known to the skilled in electrochemistry. Among these are water and polar organic solvents such as N,N-dimethylforamide, dimethyl sulfoxide, various nitriles, such as acetonitrile and glutaronitrile, and cyclic esters or mixtures of cyclic esters, e.g., propylene carbonate, gamma-butyrolactone, gamma-valerolactone, and any homogeneous mixture of any two or more of said solvents or any one or more of said solvents with ethylene carbonate. Also suitable may be mixtures of any of the above solvents The solvent will typically be liquid at room temperature. The most preferred solvent is neat propylene carbonate. Reference to "consisting essentially of" with reference to a particular solvent composition means that the solvent composition might include small amounts of other substances, such as other solvents, which do not significantly affect the properties of the solvent composition.

An anodic electrochromic compound is one which, in the solvent in its zero-potential, equilibrium state, can be electrochemically oxidized and, upon oxidation, will change (and preferably increase) its molar extinction coefficient at at least one wavelength in the visible light range. The anodic electrochromic material upon electrochemical oxidation will preferably change from having relatively low or zero to having relatively high molar extinction coefficients at some wavelengths in the visible light range, i.e., the compound preferably will change from being relatively colorless or colorless to being relatively colored upon electrochemical oxidation. The anodic electrochromic compound preferably will be stable over a wide temperature range in solution in all of its useful oxidation states both with respect to unimolecular degradation reaction and with respect to degradative reactions with other solution constituents The oxidation potential of the anodic electrochromic compound preferably will be such that little or no spontaneous oxidation of the compound takes place when the compound is dissolved in a solution comprised of a solvent and a salt of the cation of Formula IV and optionally also comprised of an inert, current-carrying electrolyte, a thickening agent, or a UV-stabilizing compound. Preferred anodic electrochromic compounds are 5,10-dihydro-5,10-dimethylphenazine, N,N,N'.N'-tetramethyl-p-phenylenediamine, N,N,N',N'-tetraphenyl-p-phenylenediamine, and bis-3,3'-diethyl-2,2'-benzothiazole azine.

In order for electrochemical oxidation to take place with a solution of the invention, the solution will necessarily have some ionic conductivity. This ionic conductivity can be provided by one or both of the electrochromic compounds themselves, if charged, or one or more dissolved, inert current-carrying, electrolyte materials (as described, for example, in the U.S. Pat. No. '108), or any combination of the above.

The bipyridinium cations employed in the present invention, e.g., those of Formula IV, are used in the form of salts of various anions One or more than one type of anion can be associated with each cation. Examples of anions that might be used to form such salts are anions such as $BF_4^-$, $PF_6^-$, $ClO_4^-$, $NO_3^-$, $SO_4^-$, $PO_4^-$, $Cl^-$, $Br^-$, and $I^-$. Preferred anions are $BF_4^-$, $PF_6^-$, $ClC_4^-$; most preferred is $BF_4^-$.

The solutions of the invention may also include thickeners, such as polymethylmethacrylate ("PMMA"), thickener derived from acrylic resin beads or sheet material (see the U.S. Pat. No. '108), polyethylene oxide ("PEOX"), or other eleotrochemically inactive polymers which are soluble in the solvent of the solution Most preferred is polymethylmethacrylate at between about 1 wt. % and 10 wt. % in the solution.

The solutions of the invention may also optionally comprise a UV-stabilizing compound or agent, such as such an agent known in the art for stabilizing plastics against degradation on exposure to UV-light, as from the sun or other sources. Among such UV-stabilizing agents which can be employed to obtain exceptional stability against UV degradation are many that are commercially available, such as the compound ethyl 2-cyano-3,3-diphenyl acrylate, sold by BASF (Parsippany, N.J., USA) under the trademark Uvinul N-35 and by Aceto Corporation (Flushing, N.Y., USA) under the trademark Viosorb 910; the compound 2-ethylhexyl-2-cyano-3,3 diphenyl acrylate, sold by BASF under the trademark Uvinul N-539; the compound 2-(2-hydroxy-4-methyl-phenyl)benzo[d]triazole, sold by Ciba-Geigy Corporation under the trademark Tinuvin P; the compound 2-hydroxy-4-methoxybenzophenone, sold by American Cyanamid under the trademark Cyasorb UV9; and the compound 2-ethyl-2'-ethoxyoxalanilide, sold by Sandoz Color & Chemicals under the trademark Sanduvor VSU. The UV-stabilizing agents or compounds will, if present, typically be present at between about 0.01M and 1.0M, more preferably at between about 0.04M and 0.7M. The more preferred UV stabilizing agents are alkyl esters of 2-cyano-3,3-diphenyl acrylic acid; most preferred is the ethyl ester.

One surprising discovery underlying the present invention is that the solutions of the invention, particular those with cations of Formula IV wherein $R_9$, $R_{10}$, $R_{11}$, and $R_{12}$ are alkyl, when employed as media of reversibly variable transmittance in solution-phase electrochromic devices, are significantly more stable to exposure to UV-radiation than such solutions with viologens, and particularly benzyl viologen. Indeed, in some applications, with a salt of a cation of Formula IV as the cathodic compound, a UV-stabilizing agent is not required.

Several methods are available in the art to prepare salts of the cations of Formula IV. When $R_9$ and $R_{10}$ are the same, $R_{11}$ and $R_{12}$ are the same, and $R_7$ and $R_8$ are the same, one method of preparation begins with the compounds of Formula V:

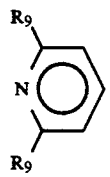

or Formula VI:

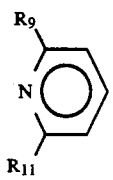

wherein $R_9$ and $R_{11}$ are defined as in Formula IV. The compounds of Formulas V and VI are available or readily synthesized by long known methods from starting materials that are commercially available.

Following one of several procedures known in the art (e.g., that of Hunig and Wehner Synthesis (1989), 552 or Baines and Campbell, U.S. Pat. No. 3,227,723), a compound of Formulas V or VI is reacted under nitrogen or another inert gas with a finely divided dispersion of sodium metal in a dry, inert solvent. This is followed by reaction with an oxidizing agent, such as oxygen or sulfur dioxide. After the oxidation, the desired 4,4'-bipyridine product is isolated from the mixture by application of various solvent extraction, fractional distillation, recrystallization and chromatographic techniques well known to the organic chemist.

Once the 4,4'-bipyridine derivative is obtained, it is taken up in a suitable organic solvent, such as acetonitrile, isopropyl alcohol, N,N-dimethylforamide or the like, and reacted at between about 60° C. and about 120° C. (e.g., at refluxing temperature if the solvent is acetonitrile) with a compound of Formula VIII $$R_7X_7 \qquad \text{VIII}$$

typically in ratio of at least 4 moles of compound of Formula VIII to 1 mole of the 4,4'-bipyridine. In Formula VIII, $R_7$ is alkyl or benzyl and $X_7$ is a good leaving group such as iodine, bromine, or the like. This reaction will provide a cation of Formula IV wherein $R_9$ and $R_{10}$ are the same, and $R_{11}$ and $R_{12}$ are the same and wherein $R_7$ and $R_8$ are the same and the same as $R_7$ of Formula VIII and wherein the cation of Formula IV is a salt of the anion $X_7$. The reaction with $R_7X_7$ is continued for between about 12 and about 250 hours. The salt of the desired cation of Formula IV will generally be present as a precipitate at the end of the reaction and can be readily filtered off, washed with the reaction solvent, and the wet filter cake dissolved in water.

A desired salt of the cation of Formula IV is prepared, from the salt obtained from the reaction in which the cation is synthesized, by simply taking the aqueous solution of the salt from the reaction and combining it with a saturated aqueous solution of a water soluble salt of the desired anion. The salt formed by the desired cation with the desired anion will then be obtained as a precipitate from the combined solutions. The precipitate can be isolated, washed, purified and dried using standard techniques to obtain a compound suitable for use as a cathodic electrochromic compound in a solution of the invention.

Preparation of salts of cations of Formula IV wherein $R_9$, $R_{10}$, $R_{11}$, and $R_{12}$ are not the same can be prepared by the method of J. A. Baltrop and A. C. Jackson, J. Chem Soc. Perkin Trans 11 (1984) 367–371. Compounds of Formula XVI

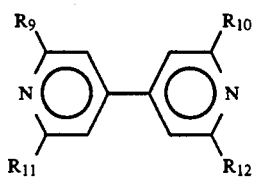

are prepared by reaction of 4,4'-bipyridine with carboxylic acids of Formula IX $$R_{15}COOH \qquad \text{IX}$$

wherein $R_{15}$ is alkyl of one to four carbons. The carboxylic acid of choice is dissolved along with 4,4'-bipyridine in an aqueous solution containing sulfuric acid and silver nitrate and the reaction solution is heated to a temperature between about 60° C. and the temperature at which the solution refluxes. Then solid ammonium persulfate is added, and the reaction is allowed to occur for from about 30 minutes to about 8 hours. A mixture of compounds is formed containing: 2-alkyl-4,4'-bipyridine, 2,2'-dialkyl-4,4'-bipyridine, 2,2',6-trialkyl-4,4'bipyridine, and group is $R_{15}$. The mixture of compounds is extracted with diethyl ether from the aqueous solution after the solution has been made alkaline. The ether is removed by evaporation and the residue is taken up in chloroform. The compounds are separated from each other and undesirable byproducts by column chromatography on a column packed with alumina and eluted with 2% ethylacetate in diethyl ether. Fractions of the eluted materials containing a particular alkylated bipyridine are combined and the solvent is removed by evaporation. Mixed alkyl substituents are obtained by reacting mono-,di-, and tri-alkylated bipyridines with compounds of Formula IX where $R_{15}$ is a different length alkyl chain than that which was reacted with the 4,4'-bipyridine initially. By this method it is possible to obtain compounds of Formula IV in which $R_9$, $R_{10}$, $R_{11}$, and $R_{12}$ are the same or different and are hydrogen or alkyl of 1 to 4 carbons with at least one of $R_9$, $R_{10}$, $R_{11}$, and $R_{12}$ being alkyl.

The compounds of Formula XVI are reacted with compounds of Formula VIII by the procedure previously given to produce compounds of Formula IV wherein $R_7$ and $R_8$ are the same and where $R_9$, $R_{10}$, $R_{11}$, and $R_{12}$ are the same or different, at least one of which is alkyl.

Compounds of Formula IV wherein $R_7$ is not the same as $R_8$ but both are alkyl of 1 to 20 carbons or benzyl are prepared by first reacting a compound of Formula VIII with the 4,4'-bipyridine, which is the same as the cation of Formula IV except that $R_7$ and $R_8$ are replaced with hydrogen, with a mole ratio of one of the bipyridine derivatives to one mole or less of compound of Formula VIII. The reaction is carried out by dissolving both compounds in a suitable solvent, such as acetonitrile, isopropyl alcohol, N,N-dimethylformamide or the like and allowing the compounds to react at a relatively low temperature of about 0° C. to about 50° C. This reaction will form a monocation where the alkyl or benzyl group of the compound of Formula VIII is bonded to only one of the nitrogens of the bipyridine. This monocation salt can be removed by filtration, washed with cold reaction solvent and placed in a second reaction with the same solvent but with a compound of Formula XI $$R_8X_8 \qquad XI$$

wherein $R_8$ is alkyl or benzyl and is different than $R_7$ and $X_8$ is a good leaving group such as iodine, bromine or the like. This second reaction is heated to between about 60° C. and about 120° C. for between 12 and about 250 hours. The precipitate present at the end of this reaction is the $X_7$ and $X_8$ salt of the cation of Formula IV with $R_7$ different from $R_8$. The precipitate can be collected, washed, dissolved in water and converted to the salt of the desired anion by the procedure described about for compounds of Formula IV with $R_7$ equal to $R_8$.

Compounds of Formula IV with $R_7$ and/or $R_8$ equal to phenyl are prepared by a method similar to that of B. Emmert and J. Stawitz, Chemishe Berichte, 56, 83-91 (1923). A 4,4'-bipyridine of Formula XVI, or a cation corresponding to such bipyridine in which one of the nitrogens has been quaternarized by reaction with a compound of Formula VIII, is reacted with a 1-halo-2,4-dinitrobenzene in a solvent like isopropyl alcohol or acetonitrile at reflux. The intermediate formed is isolated, washed and reacted with aniline in the same solvent at reflux. This yields a salt of a cation of Formula IV which is derivatized with phenyl at either or both of the 1 and 1' nitrogens. The salt can be converted to the salt of the desired anion by the procedure given above.

Solutions of the invention are readily prepared by simply dissolving the required solutes in the preselected solvent, usually at room temperature, to the desired concentration. The concentration of cathodic compound in a solution to be used for variable transmittance in a solution-phase electrochromic device will usually be from about 0.001M to about 0.1M or the solubility of the cathodic compound in the solvent of interest. Thus, solutions, which comprise anodic compounds and wherein salts of cations of Formula IV are cathodic electrochromic compounds, are straightforwardly prepared, generally as described in the U.S. Pat. No. '108.

In the solutions of the invention, which comprise an anodic compound, it is preferred but not necessary that the anodic compound have two chemically reversible oxidation waves and the cathodic compound have two chemically reversible reduction waves in the solvent of the solution in voltammograms done at room temperature.

In addition to thickener and UV-stabilizing agent, as described above, another component which a solution of the invention may optionally include is an inert, current-carrying electrolyte, of which many are known in the art and described in the U.S. Pat. No. '108.

In cases where the anodic compound, or solutions of the anodic together with cathodic compound, may be air-sensitive or otherwise unstable unless isolated from the air, as in an electrochromic device, it is preferable to prepare a solution of the invention, just prior to using the solution to fill an electrochromic device, by combining a first solution, which comprises cathodic but no anodic compound, with a second solution, which is the same as the first solution except that it comprises anodic but no cathodic compound; the examples below include examples of this procedure when the anodic compound is 5,10-dihydro-5,10-dimethylphenazine. Thus, solutions of the invention which comprise solvent and a cathodic compound, but not necessarily an anodic compound, are intermediates for preparing solutions which comprise both anodic and cathodic compounds.

Construction of solution-phase electrochromic devices in which an improved solution of the invention can be used as the medium of reversibly variable transmittance, is described in the U.S. Pat. No. '108. The preferred construction of the solution-phase electrochromic device comprises two spaced apart planar sheets of glass, each coated on the surfaces facing each other with a transparent electrode layer of indium-tin oxide or fluorine-doped tin oxide. The preferred method of providing the spacing between the planar sheets and providing the seal which, along with the electrode layers, defines the volume of the solution contained in the solution-phase device is by placing a gasket strip of uncured, thermal-cure epoxy containing glass bead spacer materials on the transparent electrode layer near the perimeter and nearly all the way around the perimeter of one of the planar sheets of glass. The second planar sheet is placed on top of the gasket strip and pressed until the uncured epoxy strip flows out and the transparent electrode layers are both in contact with the space defining glass beads. The planar glass sheets are offset from each other when the two sheets are placed together so that offset areas of transparent electrode layers extend outside the seal strip and are available for making electrical contact to the electrode layers. Contact is preferably provided with a multi-tooth spring clip or clamp.

Preferably, once the two planar glass sheets are placed together and pressed, the epoxy is cured by heating the assembly. After cooling, the parts are filled with the improved solutions of the invention by a vacuum filling process through the small void left in the gasket seal. Finally the small void in the gasket seal is plugged with a UV-cure adhesive which is then cured by exposure to UV-light.

Solution-phase electrochromic devices of the invention, containing solutions of the invention that are to be used as rearview mirrors for motor vehicles will have the construction described above in which one of the transparent electrode layers is replaced by a metal layer which serves both as an electrode and a reflector surface or, more preferably, will have the construction described above with both electrode layers being transparent and a conventional silvered mirror structure adhered adjacent to one of the planar sheets of glass on the side opposite the transparent electrode layer. This will allow the light to enter the device through one of the planar sheets of glass, pass through the first transparent electrode, through the solution layer of reversibly variable transmittance, (where a variable portion of the light may be absorbed depending on the voltage applied to the device), through the second transparent electrode, through the second planar sheet of glass, then be reflected by the silvered mirror structure and pass back out of the device with a variable portion of the reflected light being absorbed on passing back through the solution layer of reversibly variable transmittance.

Such rearview mirrors are desirable for use as dimmable, glare-relieving, rearview mirrors for motor vehicles. Solution-phase electrochromic devices of the invention, containing solutions of the invention have been found to be highly suitable for use as dimmable, glare-relieving, rearview mirrors for use on the outside of motor vehicles because of their exceptional stability to UV-light from sunlight. It has been discovered for solution-phase electrochromic devices for such use as dimmable outside rearview mirrors for motor vehicles that the sheet resistance of the transparent electrode layer(s) should be from about 1 to 40 ohms per square and that the spacing between the electrode layers in which the solution is contained should be from about 0.008 to about 0.018 centimeters for commercially acceptable performance, in uniformity of coloration, speed on dimming and clearing, and range of reflectance achievable.

U.S. Pat. No. 4,917,477, the entire disclosure of which is also incorporated herein by reference, provides disclosure by which to operate dimmable, rearview motor vehicle mirrors of the present invention, which comprise solution-phase electrochromic devices of the present invention as components of variable transmittance/reflectance.

While single-compartment and self-erasing electrochromic devices, which comprise both cathodic and anodic electrochromic compounds or substances in solution in a single compartment, are the preferred solution-phase devices contemplated for the present invention, other types of solution-phase electrochromic devices can be encompassed by the invention. For example, a device may have an anodic compound in a compartment separate from that holding the cathodic, so that oxidized anodic compound and reduced cathodic compound do not react with one another in solution to regenerate the respective zero-potential, equilibrium forms. Alternatively, an anodic compound, that is oxidized in operation of the device, might not be in solution in the device but might persist, in some solid or insoluble form, in both the oxidized and zero-potential, equilibrium states; then the cathodic compound, in reduced form in solution that is in contact with the anodic compound, might simply interact with the anodic compound in oxidized form, somewhat like interacting with an anode, to react to regenerate the zero-potential equilibrium form of the cathodic compound. Persons of skill in the electrochromics art will recognize still other types of solution-phase electrochromic devices.

The invention is described in somewhat more detail in the following, non-limiting examples. "Room temperature" means 20° C.-27° C., typically 23° C.-25° C. Unless otherwise specifically noted, all volumes and concentrations described herein are at room temperature.

EXAMPLE 1

Solution-Phase Electrochromic Devices with Salts of 1,1'-Dibenzyl-2,2',6,6'-Tetramethyl-4,4'-Bipyridinium Dication 2,2',6,6'-tetramethyl-4,4'-bipyridine is a known compound. See U.S. Pat. No. 3,227,723. 100 g of the compound was prepared from 2,6-dimethylpyridine following the method of Hunig and Wehner, Synthesis (1989), 552, using tetrahydrofuran as solvent and sulfur dioxide as oxidizing agent.

12 g of 2,2',6,6'-tetramethyl-4,4'-bipyridine and 27 ml of benzyl bromide were dissolved in 200 ml of acetonitrile and the solution was refluxed at atmospheric pressure for 96 hours. Then 40 ml of benzyl bromide was added to the solution and refluxing at atmospheric pressure was continued for an additional 48 hours. Finally, 30 ml of benzyl bromide was added to the solution and refluxing at atmospheric pressure was continued for a further 96 hours. A yellow precipitate was formed during the reaction. The precipitate was analyzed by high pressure liquid chromatography and found to be predominantly the desired 1,1'-dibenzyl-2,2',6,6'-tetramethyl-4,4'-bipyridinium dibromide.

The yellow precipitate was washed with acetonitrile and acetone, dried, dissolved in water and carbon-treated. The carbon was removed by filtration. To 700 ml of the aqueous solution, 100 ml of a saturated aqueous solution of $NaBF_4$ was added. The desired, title product precipitated. The precipitate was dissolved in 700 ml of hot water, purified by carbon treatment followed by filtration to remove the carbon, and allowed to recrystallize as the water cooled. A second recrystallization from 600 ml of water, followed by filtration and drying, yielded 8.7 g of the title product.

Elemental analysis confirmed that the product was the desired, title compound: Cal'd: C: 59.2, H: 5.3, N: 4.9, B: 3.8, F: 26.8; Found: C: 59.5, H: 5.4, N: 4.9, B:3.7, F: 19.7.

The product from the recrystallization was dried and then used to prepare, with neat propylene carbonate as solvent, a 0.01M solution with 0.5M tetra-n-butylammonium perchlorate as supporting electrolyte. An electrode was placed in the solution and polarized with respect to a counter electrode to a potential sufficient to electrochemically reduce the 1,1'-dibenzyl-2,2',6,6'-tetramethyl-4,4'-bipyridinium dication to the cation radical, as indicated by formation of a dark blue color at the cathode. A cyclic voltammogram at room temperature of this solution after a small amount of dibenzylviologen difluoroborate had been added showed that the title compound had a reduction peak potential of about 90 millivolts more negative than that of the dibenzylviologen.

A solution of 0.032M 1,1'-dibenzyl-2,2',6,6'-tetramethyl-4,4'-bipyridinium difluoroborate, 0.032M 5,10-dihydro-5,10-dimethylphenazine, 0.5M ethyl 2-cyano-3,3-diphenyl acrylate, and 3 wt. % polymethylmethacrylate ("PMMA") in propylene carbonate was prepared as follows as the solution of reversibly variable transmittance for use in a solution-phase electrochromic device. A solution was prepared by dissolving ethyl 2-cyano-3,3-diphenyl acrylate (Viosorb 910, Aceto Corporation) to 0.5M in neat propylene carbonate at room temperature. The solution was then thickened by combining with an aliquot of it 3 % (w/w) of PMMA beads and stirring at 60° C. until the beads dissolved completely. The thickened solution was then cooled to room temperature and divided into two parts. 1,1'-dibenzyl-2,2',6,6'-tetramethyl-4,4'-bipyridinium difluoroborate was dissolved to 64 mM at room temperature in one of the parts and 5,10-dihydro-5,10-dimethylphenazine was dissolved to 64 mM at room temperature in the other part. Just prior to use to fill devices, the final solution of reversibly variable transmittance was prepared by mixing equal volumes of the two parts. The final solution was then used to fill a number of devices, which were single-compartment and self-erasing (see the U.S. Pat. No. '108). The devices were suitable for use as the components of reversibly variable transmittance in variable reflectance mirrors, as each had an highly reflecting (silvered) surface adhered adjacent the outside of one of its electrode-layer-bearing walls. The electrode layers of the electrode-layer-bearing walls of the devices were transparent, made of indium-tin oxide, had a sheet resistance of about 12 ohms per square, were substantially planar and parallel (like the sheets of glass to which they were adhered), and were spaced apart by about 0.013 cm. The performance of the devices was excellent for outside motor vehicle rearview mirror use with respect to speed and uniformity of coloration and clearing and range of reflectance. One of the devices was heated without applied potential at 100° C. for 24 hours without the formation of residual color or loss in the range of reflectance attainable with the device due to degradation of the solution. Several of the devices were cycled 35,000 times at 50° C., between high reflectance with 0.0 volts applied between the electrode layers, for 15 sec./cycle, and low reflectance with 1.0 volts applied between the electrode layers, for 10 sec./cycle. The devices showed essentially no degradation in performance after the 35,000 cycles other than a decrease of about 1 % in the high-end reflectance (i.e., reflectance at 0.0 volts) measured with the standard CIE curve white light.

EXAMPLE 2

Solution Phase Electrochromic Devices with 1,1'-dibenzyl-2,2'-dimethyl-4,4'-bipyridinium difluoroborate The known compound, 2,2'-dimethyl-4,4'dipyridine, was refluxed with benzyl bromide in acetonitrile for 19 hours. The resulting 1,1'-dibenzyl-2,2'-dimethyl-4,4'-bipyridinium bromide formed a precipitate, which was filtered off, purified and converted to the difluoroborate salt by the procedure of Example 1.

A solution of 0.064M 1,1'-dibenzyl-2,2'dimethyl-4,4'-bipyridinium difluoroborate and 3 wt % PMMA in neat propylene carbonate was prepared and mixed with a solution of 0.064M 5,10-dihydro-5,10-dimethylphenazine and 3 wt. % PMMA in propylene carbonate to provide a solution of variable transmittance for solution-phase electrochromic devices. The mixing was carried out just prior to using the final solution to fill several devices. Some of the resulting devices were the components of variable transmittance in variable reflectance mirrors, and some were such components in variable transmittance windows. The devices, like those described in Example 1, had planar, parallel electrode layers of indium-tin oxide, with sheet resistance of about 12 ohms per square, on glass, with the electrode layers spaced apart by about 0.013 cm. One of the windows was measured to have a CIE curve white light transmittance of 85.0% in its zero-potential equilibrium state. When 1.0 volts was applied to the indium-tin oxide electrodes of the electrochromic device of the window, the window became uniformly blue-gray in color and a reduction in CIE curve white light transmittance to 5.5% was achieved. The stability of the solution in one of the windows on exposure to UV-light is described in Example 5 and shown in FIG. 1.

EXAMPLE 3

Solution Phase Electrochromic Devices with 1,1'-diethyl-2,2',6,6'-tetramethyl-4,4'-bipyridinium difluoroborate The title compound was made by following a procedure similar to that of Example 1 with ethyl iodide in place of benzyl bromide. Thus, 3 g of 2,2',6,6'-dipyridine and 4.5 ml of ethyl iodide were refluxed in 50 ml of acetonitrile for 72 hours. Then an additional 25 ml of ethyl iodide were added and refluxing was continued for 24 additional hours. Finally, 20 more ml of the ethyl iodide were added and the refluxing continued for 48 more hours. The desired product was present as a precipitate. Thus, the precipitate was removed by filtration and the title product was purified and converted to the difluoroborate salt as described in Example 1.

The procedure of this Example was also employed to prepare 1,1'-di-n-butyl-2,2',6,6'-tetramethyl-4,4'bipyridinium difluoroborate.

The title compound was used, together with 5,10-dihydro-5,10-dimethylphenazine and in place of 1,1'-dibenzyl-2,2',6,6'-tetramethyl-4,4'-bipyridinium difluoroborate, to make devices like those described in Example 1. The devices with the 1,1'-ethyl derivative were nearly as good as those of Example 1, except that heating the devices with the 1,1'-diethyl compound at 100° C. for 24 hours caused the formation of a residual blue color and a significant loss in high-end reflectance and, therefore also, range of reflectance.

EXAMPLE 4

Solutions of reversibly variable transmittance for solution-phase electrochromic devices A solution was prepared by dissolving ethyl 2-cyano-3,3-diphenyl acrylate (Viosorb 910) to 0.5M in neat propylene carbonate. The solution was then thickened by combining with it 3% (w/w) of PMMA beads and stirring at 60° C. until the beads dissolved completely. The thickened solution was then cooled to room temperature and divided into four parts of equal volume. 1,1'-dibenzyl-2,2',6,6'-tetramethyl-4,4'-bipyridinium difluoroborate was dissolved to 0.064M in one of the four parts and 0.056M in another. 5,10-dihydro-5,10-dimethylphenazine was dissolved to 0.064M in one of the four parts and 0.056M in another. Then, just prior to being used to fill single-compartment, self-erasing, solution-phase electrochromic devices, one solution of variable transmittance was made by combining equal volumes of the solutions with 0.064M of the bipyridinium salt and 0.064M of the dimethylphenazine, respectively, to provide a solution with the electrochromic compounds at 0.032M, and another solution of variable transmittance was made by combining equal volumes of the solutions with 0.056M of the bipyridinium salt and 0.056M of the dimethylphenazine, respectively, to provide a solution with the electrochromic compounds at 0.028M.

The resulting solutions of reversibly variable transmittance were used to fill several, differently sized solution-phase electrochromic devices, which were single-compartment, self-erasing, solution-phase electrochromic devices similar to those described in the U.S. Pat. No. '108. The devices comprised two walls made of clear glass 0.21 cm thick and having on the inside surfaces (i.e., the surfaces facing one another and defining walls of the single compartment) an electrode layer of indium-tin oxide with a sheet resistance of about 12 ohms per square. Some of the devices, used as components of reversibly variable transmittance in variable reflectance mirrors, had a highly reflecting layer of silver affixed adjacent one of the glass walls on the side opposite the electrode layer. The electrode layers, like the clear glass walls to which they were affixed, were substantially transparent (to CIE curve white light) and substantially planar and parallel.

The smaller area devices, some of which were suitable for use as components of variable transmittance in small, outside, variable-reflectance, rearview mirrors on motor vehicles, were nearly rectangular, with the shorter dimension of the glass-wall surface less than 10 cm. This shorter dimension is generally the height, i.e., oriented approximately vertically in a mirror as installed in a motor vehicle, and is also a variable that is pertinent to speed and uniformity of darkening because it is approximately the same as the distance (nearly vertical in installed mirrors) between the clip contacts through which current is supplied to the electrode layers of the devices. These smaller devices (<about 10 cm in shorter dimension and distance between clip contacts) had the electrode layers spaced apart by 0.013 cm and were filled with the solution described above with the electrochromic compounds at 0.032M.

The larger area devices were suitable for use as components of variable transmittance in larger, outside, variable-reflectance, rearview mirrors on motor vehicles. These larger devices were nearly rectangular with the shorter dimension of the glass-wall surface (and distance between clip contacts) greater than about 10 cm. These larger devices had the electrode layers spaced apart by 0.014 cm and were filled with the solution described above with the electrochromic compounds at 0.028M.

The electrode layer spacings, concentrations of electrochromic materials and electrode sheet resistances were chosen empirically to provide variable reflectance, rearview, automobile mirrors with commercially acceptable speed and uniformity of coloring and clearing and range of reflectance.

When the devices were activated to their colored states by application of a voltage between the indium-tin oxide electrodes, the mirrors became colored with a color that were more nearly pure blue than the green-blue of mirrors that are the same but have benzylviologen (i.e., 1,1'-dibenzyl-4,4'bipyridinium) difluoroborate rather than 1,1'-dibenzyl-2,2',6,6'-tetramethyl-4,4'-bipyridinium difluoroborate in the solution of variable transmittance in the electrochromic device. The color and its intensity in the devices, at useful operating voltages in the range of 0.4 volts to at least 1.4 volts, in the mirrors with the 1,1'-dibenzyl-2,2',6,6'-tetramethyl-4,4'-bipyridinium cation, are certainly commercially acceptable for use in motor vehicle mirrors. Further, the fact that the color of the mirrors with the 1,1'-dibenzyl-2,2',6,6'-tetramethyl-4,4,-bipyridinium dication and 5,10-dihydro-5,10-dimethylphenazine is more nearly blue makes such mirrors somewhat more desirable commercially than the mirrors with the benzylviologen dication and 5,10-dihydro-5,10-dimethylphenazine.

EXAMPLE 5

A number of tests are employed to evaluate the suitability of compounds, as anodic electrochromic compounds or cathodic electrochromic compounds, and solutions of differing compositions, as solutions of reversibly variable transmittance, in single-compartment, solution-phase, self-erasing electrochromic devices.

A basic factor related to such suitability is the solubility of the compound, in its zero-potential, equilibrium state and its oxidized (in the case of an anodic compound) or reduced (in the case of a cathodic compound) state in the solvent of the solution. It is generally preferable, in an electrochromic device, to have the solution of reversibly variable transmittance present in only a thin layer, typically between about 0.001 cm and 0.1 cm in thickness, and, at the same time, to have as large as possible a difference between the transmittance over the entire visible range, i.e., of CIE white light, through the device when it is operated (i.e., a potential is applied between the electrode layers) and when it is in the zero-potential equilibrium state. For devices used in various window applications, it is desireable to have electrochromic compounds with solubilities in suitable solvents between about 0.001M and about 0.01M For a solution layer thickness of about 0.013 cm, it is desireable to have a cathodic compound with a solubility at room temperature of at least about 0.005M, and preferably at least 0.025M, when used with 5,10-dihydro-5,10-dimethylphenazine at the same concentration as the cathodic compound. Table 1 shows solubilities for several compounds of Formula IV.

TABLE 1

Solubilities in Propylene Carbonate of Various Cathodic Compounds with Cations of Formula XX $$R_{21}-{}^+N\underset{R_{24}}{\overset{R_{22}}{\diagup\bigcirc\diagdown}}\underset{R_{25}}{\overset{R_{23}}{\diagup\bigcirc\diagdown}}N^+-R_{21} \quad XX$$

| $R_{21}$ | $R_{22}, R_{24}{}^1$ | $R_{23}, R_{25}{}^1$ | Anion | Solubility (Molar) |
|---|---|---|---|---|
| methyl | methyl | methyl | $I^-$ | <0.01 |
| methyl | methyl | methyl | $BF_4{}^-$ | >0.005 but <0.01 |
| methyl | methyl | methyl | $ClO_4{}^-$ | <0.01 |
| methyl | methyl | methyl | $PF_6{}^-$ | <0.01 |
| ethyl | methyl | methyl | $BF_4{}^-$ | >0.03 but <0.06 |
| n-butyl | methyl | methyl | $BF_4{}^-$ | >0.06 |
| benzyl | hydrogen | hydrogen | $BF_4{}^-$ | >0.06 |
| benzyl | methyl, hydrogen | methyl, hydrogen | $BF_4{}^-$ | >0.06 |
| benzyl | methyl | methyl | $I^-$ | >0.03 but <0.06 |
| benzyl | methyl | methyl | $BF_4{}^-$ | >0.06 |

[1] If one substituent is indicated, both substituents are the same. If two substituents are indicated, the two substituents are different.

Another measure of the suitability of a compound for use as an anodic or cathodic electrochromic compound is the stability of the compound at high temperature in a solvent, as used in a solution of reversibly variable transmittance. This is because electrochromic devices are often exposed to high temperatures, e.g., as a consequence of exposure to sunlight as part of a window or an outside rearview mirror of an automobile or a consequence of heating as part of a mirror inside an unventilated automobile exposed to the sun. This stability can be determined by preparing a solution of the compound in a solvent and then holding the solution at a high temperature (e.g., 100° C.) for 24 hours and then ascertaining whether a change in color or transmittance has occurred, a precipitate has formed, or some other sign of instability is apparent in the solution. No discernible change (to the unaided human eye) indicates good thermal stability. Slight change (e.g., slight change in color, no precipitate), observable with the unaided human eye, indicates fair thermal stability. A major change (e.g. major change in color or transmittance or formation of a precipitate), observable with the unaided human eye, indicates poor thermal stability. Such tests for stability at 100° C. were carried out with solutions of the compounds indicated in Table 2 in propylene carbonate.

TABLE 2

Thermal Stability in Propylene Carbonate of Cations of Formula XX of Various Cathodic Compounds[1]

XX

[structure: R_{21}—+N(ring with R_{22}, R_{24})—(ring with R_{23}, R_{25})—N+—R_{21}]

| $R_{21}$ | $R_{22}, R_{24}$[2] | $R_{23}, R_{25}$[2] | Thermal Stability |
|---|---|---|---|
| methyl | methyl | methyl | good |
| ethyl | methyl | methyl | poor |
| n-butyl | methyl | methyl | fair |
| benzyl | hydrogen | hydrogen | good |
| benzyl | methyl, hydrogen | methyl, hydrogen | good |
| benzyl | methyl | methyl | good |

[1]Anion is $BF_4^-$ for all of the compounds.
[2]If one substituent is indicated, both substituents are the same. If two substituents are indicated, the two substituents are different.

Two measures of suitability of solutions of reversibly variable transmittance, for single-compartment, solution-phase, self-erasing electrochromic devices, are the stability of the solutions to cycling in such a device between high transmittance (e.g., the transmittance at zero-potential equilibrium) and low transmittance (e.g., the transmittance at steady state at maximum operating potential between the electrode layers), particularly at a high temperature (e.g., at about 50° C.) and the stability of the solutions to exposure to UV-radiation in the absence of cycling. Of course, if a number of such solutions, which differ only in the cation of the cathodic electrochromic compound which they employ, are tested under the same conditions for stability to cycling and stability to exposure to UV-radiation, any differences in such stability can be ascribed to the cations (or the cation radicals when reduced) of the cathodic electrochromic compounds involved.

Solutions were prepared as described in Example 4, with or without the UV stabilizing compound (ethyl 2-cyano-3,3-diphenyl acrylate), with compounds selected from those listed in Table 2 above, each at a final concentration of 32 mM. The solutions were then evaluated for stability to cycling at 50° C. or stability to exposure to UV radiation as follows: Solution-phase electrochromic devices with the construction described in Example 4, without the silvered reflector surface, were filled with the solution to be tested. The resulting devices function as electrochromic light filters (windows) and, through monitoring of the transmittance through them, can also serve to measure the stability that the solutions in the devices have or mirrors constructed with the devices would have. (The mirrors would, of course, have the silvered reflector surface or a highly reflecting electrode layer; and, with mirrors, reflectance rather than transmittance would be monitored.) The electrochromic windows, with no applied potential, were exposed to UV light from a series of mercury flood lamps. The intensity of UV-light in the 325 to 380 nm range was measured to be about 2 milliwatts per cm² at the windows. The temperature of the windows during exposure to UV light was held at about 80° C. The UV exposure was continuous other than for brief periods during which the transmittance was measured. Table 3 lists results of evaluating, using light filter-type devices, of solutions with different cathodic electrochromic compounds, with cations of Formula IV, for stability to cycling at 50° C. and stability to exposure to UV radiation at 80° C. If the CIE curve white light transmittance of electrochromic windows exposed to UV-light, as just described, remained above 70%, the stability of the solution was considered good; if above only 60%, the stability was considered fair; and if below 60 % the stability was considered poor, this being for solutions which did not contain a UV stabilizer. (The solutions listed in Table 3, when tested for UV-stability, did not include UV-stabilizer.)

If electrochromic mirrors showed a decrease in high end reflectance of CIE curve white light which was less than 5 percentage points due to cycling at 50° C. for 10 seconds with zero volts applied and 10 seconds with about 1 volt applied, the stability of the solutions due to cycling was considered good. If the reflectance decreased more than 5 percentage points, the stability was considered poor.

TABLE 3

Stability to Cycling at 50° C. and Exposure to UV Radiation of Cations of Formula XX of Various Cathodic Compounds[1]

XX

[structure: R_{21}—+N(ring with R_{22}, R_{24})—(ring with R_{23}, R_{25})—N+—R_{21}]

| $R_{21}$ | $R_{22}, R_{24}$[2] | $R_{23}, R_{25}$[2] | Stability to Cycling | Stability to UV Exposure |
|---|---|---|---|---|
| ethyl | methyl | methyl | poor | not tested |
| benzyl | hydrogen | hydrogen | good | poor |
| benzyl | methyl, hydrogen | methyl, hydrogen | good | fair |
| benzyl | methyl | methyl | good | good |

[1]Anion is $BF_4^-$ for all of the compounds. All compounds at 32 mM (room temp.) in propylene carbonate with 32 mM (room temp.) of 5,10-dihydro-5,10-dimethylphenazine as anodic compound. Some solutions also contained 3 wt. % PMMA, which is known to have no effect on stability to cycling or UV-exposure. Some of the solutions tested for stability to cycling also included 0.5M ethyl 2-cyano-3,3-diphenyl acrylate, which is known to have no effect on stability to cycling. No UV-stabilizer was included in any of the solutions tested for stability to UV exposure.
[2]If one substituent is indicated, both substituents are the same. If two substituents are indicated, the two substituents are different.

Results of testing for stability against exposure to UV-light are also illustrated in FIG. 1, wherein transmission of white light through an electrochromic device (a light filter), without applied potential, is plotted as a function of duration of exposure to UV-light for the solutions of reversibly variable transmittance without UV-stabilizing agent and with the $BF_4^-$ salts of benzyl viologen (Curve C in FIG. 1), 1,1'-dibenzyl-2,2'-dimethyl-4,4'-bipyridinium (Curve B in FIG. 1), and 1,1'-dibenzyl-2,2',6,6'-tetramethyl-4,4'-bipyridinium (Curve A in FIG. 1) as the cathodic compounds. The superiority, in stability to exposure to UV-light, of the solution with 1,1'-dibenzyl-2,2',6,6'-tetramethyl-4,4'-bipyridinium ion as the cation of the cathodic compound is readily apparent from FIG. 1.

Figure 2:
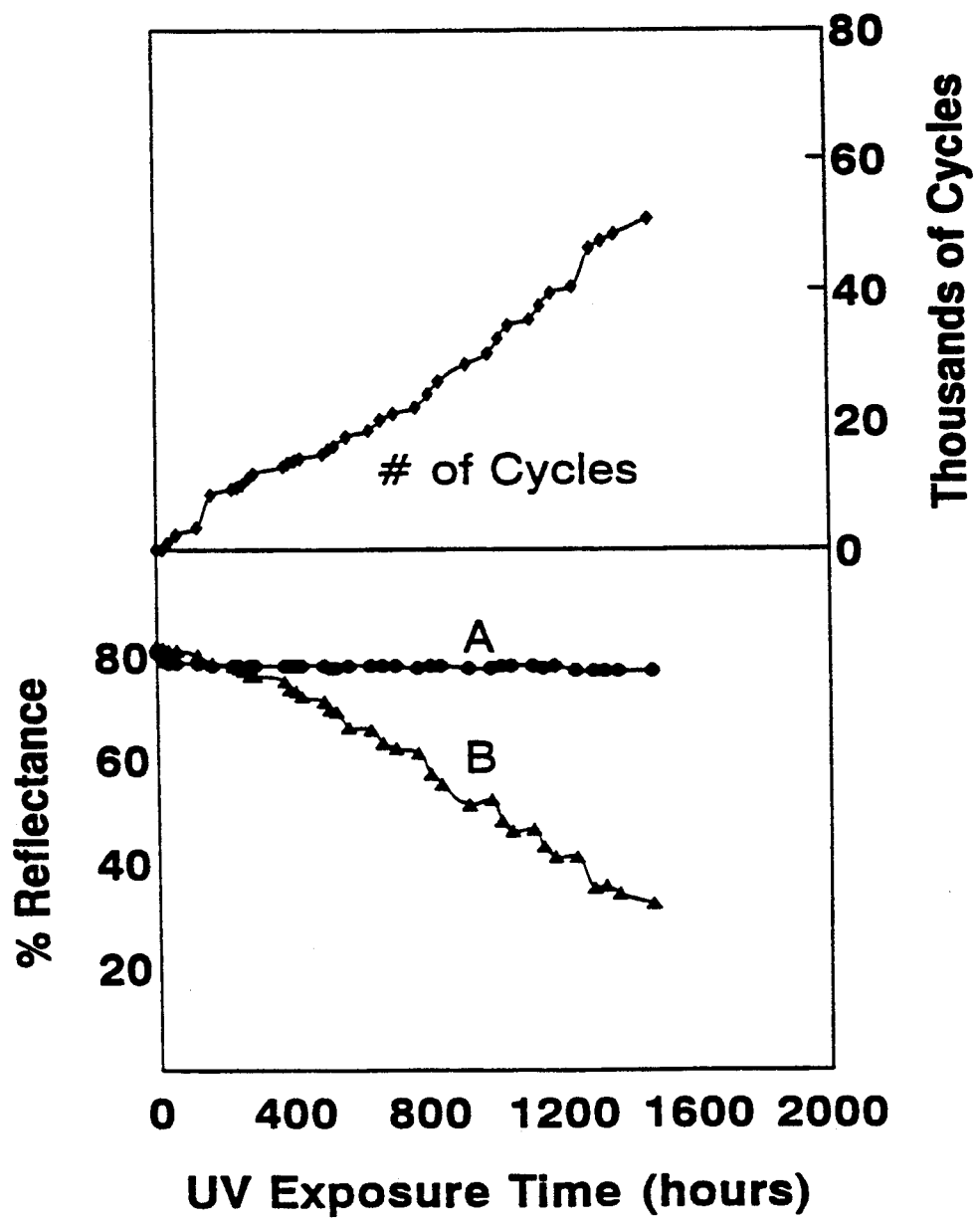
FIG. 2 is a graph illustrating the stabilities to cycling and exposure to ultraviolet radiation of solutions of 5,10-dihydro-5,10-dimethylphenazine and a UV-stabilizing compound with two different 4,4'-bipyridinium cathodic electrochromic compounds: 1,1'-dibenzyl-2,2',6,6'-tetramethyl-4,4'-bipyridinium difluoroborate (Curve A) and 1,1'-dibenzyl-4,4'-bipyridinium difluoroborate (Curve B).

A test for the stability, under conditions that mimic reasonably closely actual operating conditions, of a solution of reversibly variable transmittance in a single-compartment, self-erasing, solution-phase electrochromic device that is used to provide variable reflectance in a preferred application of the present invention, a variable-reflectance, outside, rearview motor-vehicle mirror, combines exposure to UV-light, without cycling between high (zero-potential equilibrium) and low (steady-state with applied potential) reflectance, with exposure to ambient room light (with little or no UV-light) with such cycling. This test mimics the actual conditions to which such a solution is exposed because such a mirror is usually not cycled but is exposed to UV-light (due to sunlight) during daylight hours but is cycled, to relieve glare caused by headlights of automobiles approaching from the rear, at night when almost no UV-light from the sun is present. Thus, two solutions, as described in Example 4, both with ethyl 2-cyano-3,3-diphenyl acrylate UV-stabilizer (Viosorb 910), but one with benzyl viologen (1,1'-dibenzyl-4,4'-bipyridinium) as the cation of the cathodic compound instead of 1,1'-dibenzyl-2,2',6,6'-tetramethyl-4,4'-bipyridinium, were tested in a single-compartment, solution-phase, self-erasing electrochromic device adapted as the component of reversible variable transmittance in a variable reflectance mirror (i.e., having an highly reflecting (silvered) surface adjacent the outside surface (surface not in contact with solution) of one of the transparent (glass), electrode-layer-bearing walls of the device). The mirrors were exposed to UV-light, for usually about 18 hours per day as described above, followed by cycling for usually about 6 hours in room light at room temperature between high reflectance and low reflectance. Each cycle consisted of 10 seconds with 0.0 volts applied and 10 seconds with 1.0 volt applied between the electrodes of the mirror. Results of this test are shown in FIG. 2. The number of potential-varying cycles varied somewhat during the cycling periods and are shown in the upper part of FIG. 2. The superior stability, by an unexpectedly large margin, of the solution with the 1,1'-dibenzyl-2,2',6,6'-tetramethyl-4,4'-bipyridinium cation is apparent from the curves in the lower part of FIG. 2, relating reflectance from the mirrors to UV-exposure time and, indirectly, the number of potential-varying cycles. Curve A is for the solution with the 1,1'-dibenzyl-2,2',6,6'-tetramethyl-4,4'-bipyridinium cation. Curve B is for the solution with benzyl viologen cation.

While the present invention has been described with some specificity herein, those of skill in the pertinent arts will recognize many modifications and variations of what has been described that are nonetheless within the spirit of the invention. It is intended that the invention as described and claimed encompass such modifications and variations.

What is claimed is:

1. A solution which comprises a solvent; an anodic electrochromic compound which, upon oxidation of its zero-potential equilibrium state, undergoes an increase in molar extinction coefficient at at least one wavelength in the visible range; and a cathodic electrochromic compound which is a salt of a cation of the formula

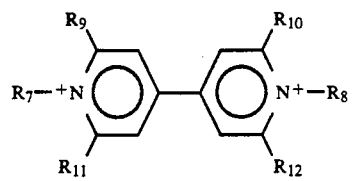

wherein $R_7$ and $R_8$ are independently selected from the group consisting of an alkyl group with 1–20 carbon atoms and benzyl; and $R_9$, $R_{10}$, $R_{11}$, and $R_{12}$ are independently selected from the group consisting of hydrogen and an alkyl group with 1–4 carbon atoms, provided that at least three of $R_9$, $R_{10}$, $R_{11}$, and $R_{12}$ are alkyl groups.

2. A solution according to claim 1 wherein the solvent is liquid at room temperature and consists essentially of a polar organic solvent or a mixture of polar organic solvents.

3. A solution according to claim 2 wherein the solvent consists essentially of propylene carbonate, gamma-butyrolactone, gamma-valerolactone, or an homogeneous mixture of any two or more of said solvents or any one or more of said solvents with ethylene carbonate.

4. A solution according to claim 3 wherein the solvent consists essentially of propylene carbonate.

5. A solution according to claim 1 wherein the anodic compound in the solution is selected from the group consisting of 5,10-dihydro-5,10-dimethylphenazine, N,N,N',N'-tetramethyl-p-phenylenediamine, N,N,N',N'-tetraphenyl-p-phenylenediamine, and bis-3,3'-diethyl-2,2'-benzothiazole azine.

6. A solution according to claim 2 wherein the anodic compound in the solution is selected from the group consisting of 5,10-dihydro-5,10-dimethylphenazine, N,N,N',N'-tetramethyl-p-phenylenediamine, N,N,N',N'-tetraphenyl-p-phenylenediamine, and bis-3,3'-diethyl-2,2'-benzothiazole azine.

7. A solution according to claim 3 wherein the anodic compound in the solution is selected from the group consisting of 5,10-dihydro-5,10-dimethylphenazine, N,N,N',N'-tetramethyl-p-phenylenediamine, N,N,N',N'-tetraphenyl-p-phenylenediamine, and bis-3,3'-diethyl-2,2'-benzothiazole azine.

8. A solution according to claim 4 wherein the anodic compound in the solution is selected from the group consisting of 5,10-dihydro-5,10-dimethylphenazine, N,N,N',N'-tetramethyl-p-phenylenediamine, N,N,N',N'-tetraphenyl-p-phenylenediamine, and bis-3,3'-diethyl-2,2'-benzothiazole azine.

9. A solution according to claim 7 wherein the anodic compound is 5,10-dihydro-5,10-dimethylphenazine.

10. A solution according to claim 8 wherein the anodic compound is 5,10-dihydro-5,10-dimethylphenazine.

11. A solution according to claim 5 wherein, in the cathodic electrochromic compound, $R_9$, $R_{10}$, $R_{11}$, and $R_{12}$ of the cation are alkyl groups, and the anions are selected from the group consisting of $BF_4^-$, $PF_6^-$ and $ClO_4^-$.

12. A solution according to claim 6 wherein, in the cathodic electrochromic compound, $R_9$, $R_{10}$, $R_{11}$, and $R_{12}$ of the cation are alkyl groups, and the anions are selected from the group consisting of $BF_4^-$, $PF_6^-$ and $ClO_4^-$.

13. A solution according to claim 7 wherein, in the cathodic electrochromic compound, $R_9$, $R_{10}$, $R_{11}$, and $R_{12}$ of the cation are alkyl groups, and the anions are selected from the group consisting of $BF_4^-$, $PF_6^-$ and $ClO_4^-$.

14. A solution according to claim 8 wherein, in the cathodic electrochromic compound, $R_9$, $R_{10}$, $R_{11}$, and $R_{12}$ of the cation are alkyl groups, and the anions are selected from the group consisting of $BF_4^-$, $PF_6^-$ and $ClO_4^-$.

15. A solution according to claim 9 wherein, in the cathodic electrochromic compound, $R_9$, $R_{10}$, $R_{11}$, and $R_{12}$ of the cation are alkyl groups, and the anions are selected from the group consisting of $BF_4^-$, $PF_6^-$ and $ClO_4^-$.

16. A solution according to claim 10 wherein, in the cathodic electrochromic compound, $R_9$, $R_{10}$, $R_{11}$, and $R_{12}$ of the cation are alkyl groups, and the anions are selected from the group consisting of $BF_4^-$, $PF_6^-$ and $ClO_4^-$.

17. A solution according to claim 11 wherein, in the cation of the cathodic electrochromic compound, both $R_7$ and $R_8$ are benzyl.

18. A solution according to claim 17 wherein, in the cathodic electrochromic compound, $R_9$, $R_{10}$, $R_{11}$, and $R_{12}$ of the cation are methyl and the anions are $BF_4^-$.

19. A solution according to claim 12 wherein, in the cation of the cathodic electrochromic compound, both $R_7$ and $R_8$ are benzyl.

20. A solution according to claim 19 wherein, in the cathodic electrochromic compound, $R_9$, $R_{10}$, $R_{11}$, and $R_{12}$ of the cation are methyl and the anions are $BF_4^-$.

21. A solution according to claim 13 wherein, in the cation of the cathodic electrochromic compound, both $R_7$ and $R_8$ are benzyl.

22. A solution according to claim 21 wherein, in the cathodic electrochromic compound, $R_9$, $R_{10}$, $R_{11}$, and $R_{12}$ of the cation are methyl and the anions are $BF_4^-$.

23. A solution according to claim 14 wherein, in the cation of the cathodic electrochromic compound, both $R_7$ and $R_8$ are benzyl.

24. A solution according to claim 23 wherein, in the cathodic electrochromic compound, $R_9$, $R_{10}$, $R_{11}$, and $R_{12}$ of the cation are methyl and the anions are $BF_4^-$.

25. A solution according to claim 15 wherein, in the cation of the cathodic electrochromic compound, both $R_7$ and $R_8$ are benzyl.

26. A solution according to claim 25 wherein, in the cathodic electrochromic compound, $R_9$, $R_{10}$, $R_{11}$, and $R_{12}$ of the cation are methyl and the anions are $BF_4^-$.

27. A solution according to claim 16 wherein, in the cation of the cathodic electrochromic compound, both $R_7$ and $R_8$ are benzyl.

28. A solution according to claim 27 wherein, in the cathodic electrochromic compound, $R_9$, $R_{10}$, $R_{11}$, and $R_{12}$ of the cation are methyl and the anions are $BF_4^-$.

29. A solution according to any one of claims 1, 8, 10, 14, 16, 23, 24, 27 and 28 wherein the concentrations of the cathodic electrochromic compound and the anodic electrochromic compound are from 0.001M to 0.1M.

30. A solution according to claim 29 which is thickened with 1 wt. %–10 wt. T polymethymethacrylate.

31. A solution according to any one of claims 1, 8, 10, 14, 16, 23, 24, 27 and 28 which comprises a UV-stabilizing compound.

32. A solution according to claim 29 which comprises, at a concentration from 0.1M to 0.6M, an alkyl ester of 2-cyano-3,3-diphenyl acrylate, wherein the alkyl group has 1-10 carbon atoms.

33. A solution according to claim 32 wherein the alkyl ester is ethyl 2-cyano-3,3-diphenyl acrylate.

34. A solution according to claim 30 which comprises, at a concentration from 0.1M to 0.6M, an alkyl ester of 2-cyano-3,3-diphenyl acrylate, wherein the alkyl group has 1-10 carbon atoms.

35. A solution according to claim 34 wherein the alkyl ester is ethyl 2-cyano-3,3-diphenyl acrylate.

36. A solution which is liquid at room temperature and comprises a solvent and a $BF_4^-$, $PF_6^-$, or $ClO_4^-$ salt of a cation of Formula XVII

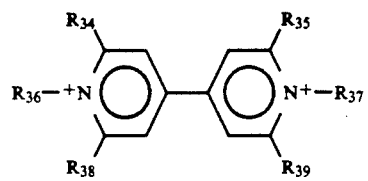

XVII wherein $R_{36}$ and $R_{37}$ independently selected from the group consisting of benzyl and alkyl of 1-20 carbon atoms; and $R_{34}$, $R_{35}$, $R_{38}$ and $R_{39}$ are independently selected from the group consisting of hydrogen and alkyl groups of 1-4 carbon atoms, provided that at least three of $R_{34}$, $R_{35}$, $R_{38}$ and $R_{39}$ are alkyl.

37. A solution of claim 36 wherein the solvent consists essentially of propylene carbonate, gamma-butyrolactone, gamma-valerolactone, or an homogeneous mixture of any two or more of said solvents or any one or more of said solvents with ethylene carbonate.

38. A solution of claim 36 wherein, in the cation of Formula XVII, $R_{36}$ and $R_{37}$ are benzyl.

39. A solution of claim 37 wherein, in the cation of Formula XVII, $R_{36}$ and $R_{37}$ are benzyl.

40. A solution of claim 38 wherein the cation of Formula XVII is 1,1'-dibenzyl-2,2',6,6'-tetramethyl-4,4'-bipyridinium.

41. A solution of claim 39 wherein the cation of Formula XVII is 1,1'-dibenzyl-2,2',6,6'-tetramethyl-4,4'-bipyridinium.

42. A solution of claim 37 wherein the solvent consists essentially of propylene carbonate, the anion is $BF_4^-$, and the concentration of the salt at room temperature is from 0.001M to 0.1M.

43. A solution of claim 39 wherein the solvent consists essentially of propylene carbonate, the anion is $BF_4^-$, and the concentration of the salt at room temperature is from 0.001M to 0.1M.

44. A solution of claim 41 wherein the solvent consists essentially of propylene carbonate, the anion is $BF_4^-$, and the concentration of the salt at room temperature is from 0.001M to 0.1M.

45. A solution of any one of claims 36-41 which comprises a compound selected from the group consisting of 5,10-dihydro-5,10-dimethylphenazine, N,N,N',N'-tetramethyl-p-phenylenediamine, N,N,N',N'-tetraphenyl-p-phenylenediamine, and bis-3,3'-diethyl-2,2'-benzothiazole azine.

46. A solution of any one of claims 42-44 which comprises, at a concentration from 0.001M to 0.1M, a compound selected from the group consisting of 5,10-dihydro-5,10-dimethylphenazine, N,N,N',N'-tetramethyl-p-phenylenediamine, N,N,N',N'-tetraphenyl-p-phenylenediamine, and bis-3,3'-diethyl-2,2'-benzothiazole azine.

47. A solution of claim 45 which comprises 5,10-dihydro-5,10-dimethylphenazine.

48. A solution of claim 46 which comprises 5,10-dihydro-5,10-dimethylphenazine.

49. A solution of claim 45 which comprises a UV-stabilizing compound.

50. A solution of claim 49 wherein the UV-stabilizing compound is an alkyl ester of-2-cyano-3,3-diphenylacrylate, wherein the alkyl group is of 1–10 carbon atoms.

51. A solution of claim 50 wherein the UV-stabilizing compound is an ethyl 2-cyano-3,3-diphenyl-acrylate.

52. A solution of claim 46 which comprises, at a concentration at room temperature between 0.1M and 0.6M, an alkyl ester of 2-cyano-3,3-diphenyl-acrylate, wherein the alkyl group is of 1–10 carbon atoms.

53. A solution of claim 47 which comprises, at a concentration at room temperature between 0.1M and 0.6M, an alkyl ester of 2-cyano-3,3-diphenyl-acrylate, wherein the alkyl group is of 1–10 carbon atoms.

54. A solution of claim 52 wherein the alkyl ester is ethyl 2-cyano-3,3-diphenyl-acrylate.

55. A solution of claim 53 wherein the alkyl ester is ethyl 2-cyano-3,3-diphenyl-acrylate.

56. A solution of claim 54 which is thickened with 1 wt. %–10 wt % polymethylmethacrylate.

57. A solution of claim 55 which is thickened with 1 wt. %–10 wt. % polymethylmethacrylate.

* * * * *